United States Patent [19]
Yamamoto et al.

[11] Patent Number: 5,488,469
[45] Date of Patent: Jan. 30, 1996

[54] CELL ANALYZING APPARATUS

[75] Inventors: Koji Yamamoto; Masahiro Hanafusa, both of Kyoto; Fumio Onuma, Kameoka; Michio Nishimura, Osaka, all of Japan

[73] Assignee: Omron Corporation, Kyoto, Japan

[21] Appl. No.: 936,680

[22] Filed: Aug. 28, 1992

[30] Foreign Application Priority Data

| Aug. 30, 1991 | [JP] | Japan | 3-219737 |
| Sep. 2, 1991 | [JP] | Japan | 3-221390 |
| May 14, 1992 | [JP] | Japan | 4-121787 |

[51] Int. Cl.[6] ................................. G01N 21/00
[52] U.S. Cl. ................................. 356/72; 356/39
[58] Field of Search ................................. 356/213, 243, 356/72, 39; 377/29; 250/458.1, 458.2, 461.1, 462.1

[56] References Cited

U.S. PATENT DOCUMENTS

| 3,412,037 | 11/1968 | Gochman et al. | 356/39 X |
| 3,973,189 | 8/1976 | Angel et al. | |
| 3,977,995 | 8/1976 | Louderback et al. | |
| 5,093,234 | 3/1992 | Schwartz | 356/213 X |

FOREIGN PATENT DOCUMENTS

| 0240942 | 4/1987 | European Pat. Off. |
| 0350837 | 7/1989 | European Pat. Off. |
| 0470810 | 8/1991 | European Pat. Off. |
| 2370276 | 11/1977 | France |
| 2165050 | 6/1990 | Japan |

Primary Examiner—Frank Gonzalez
Assistant Examiner—K. P. Hantis
Attorney, Agent, or Firm—Fish & Richardson

[57] ABSTRACT

A cell analyzing apparatus which employs flow cytometry to obtain the concentration (the cell count per unit volume) of a specimen under examination is adapted to measure either the cell count of a control specimen the concentration of which is known or the length of time the control specimen is measured. The concentration of the specimen under examination is calculated based upon the cell count thereof obtained over a length of measurement time identical with the length of measurement time of the control specimen. Alternatively, the concentration of the specimen under examination is calculated based upon the length of measurement time thereof needed to obtain a cell count identical with that of the control specimen.

10 Claims, 9 Drawing Sheets

| ANTIBODY CLASSIFICATION | POSITIVE RATIO (%) | ABSOLUTE CELL COUNT (CELLS/MM$^3$) |
|---|---|---|
| CD3 | 57~78 | 1900~6800 |
| CD4 | 34~59 | 1300~4400 |
| CD8 | 16~35 | 700~2800 |
| CD16 | 4~16 | 200~800 |
| CD19 | 17~41 | 500~2800 |

MEASUREMENT TIME →

CELL ANALYZING APPARATUS

BACKGROUND OF THE INVENTION

1. Field of the Invention

This invention relates to a cell analyzing apparatus of the type which employs flow cytometry.

2. Description of the Related Art

In flow cytometry, a sample containing cells (or particles that are the equivalent thereof) labeled or conjugated with a fluorescent dye is passed through a slender flow cell along with a sheath fluid so that the cells flow in single file. The individual cells in the flow are irradiated one at a time with a light beam such as a laser beam by means of hydrodynamic focusing, and the intensity of scattered light or fluorescent light from the cells, namely light information indicative of the cells, is measured instantaneously to analyze the cells. Flow cytometry of this kind is advantageous in that a large quantity of cells can be analyzed at high speed and with great accuracy.

A known example of a cell analyzing apparatus using such flow cytometry comprises a flow cell for forming a slender stream of liquid, a light source (such as a laser) for irradiating the cells which flow through the interior of the flow cell with a light beam, a photodetector for detecting cell light information from the cells irradiated with the light beam and converting the light information into an electric signal, a signal processing circuit for amplifying, integrating and removing noise from the signal produced by the photodetector, and a computer for processing a signal, which represents the cell light information, outputted by the signal processing circuit.

For example, when subsets of lymphocytes in blood are analyzed, a monoclonal antibody labeled with a fluorescent dye is made to react with human blood, after which a hemolytic treatment is applied. The result is used as the sample.

The sample cells which flow through the flow cell are irradiated with a laser beam and four parameters, namely forward-scattered light intensity $I_0$, 90° side-scattered light intensity $I_{90}$, green fluorescence intensity $I_g$ and red fluorescence intensity $I_r$, are detected by respective detectors, as a result of which cell light information (hereinafter referred to simply as "data" where appropriate) is obtained. Since the sample contains cells such as monocytes and granulocytes in addition to lymphocytes, it is required that the data relating to the lymphocytes be discriminated and selected from the data regarding the other cells.

Figure 11:
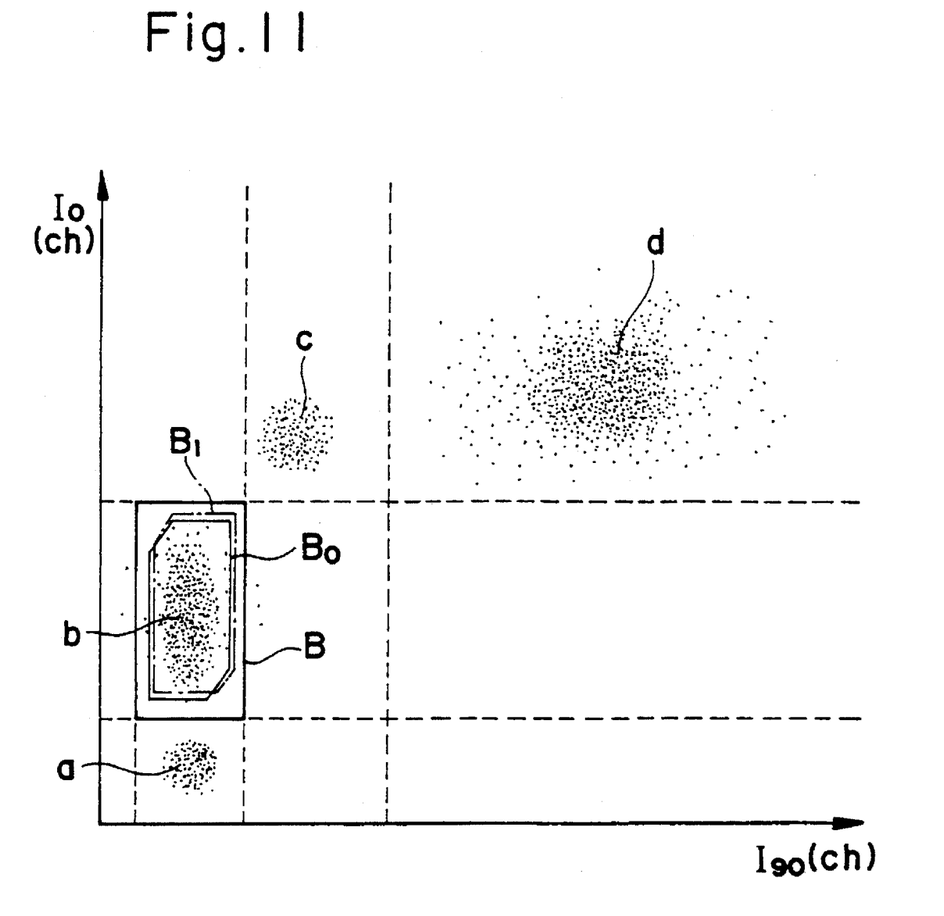
FIG. 11 is a cytogram showing 90° side-scattered light intensity $I_{90}$ plotted against forward-scattered light intensity $I_0$ for the purpose of describing various arithmetic operations.

As shown in FIG. 11, two parameters, namely forward-scattered light intensity $I_0$, which represents the size of cells, and 90° side-scattered light intensity $I_{90}$, which represents the complexity of the internal structure of cells, are used to produce a cytogram in which $I_{90}$ is plotted along the horizontal axis and $I_0$ is plotted along the vertical axis. In FIG. 11, both $I_{90}$ and $I_0$ are normalized depending upon the maximum values measured to make the maximum value on the scale 256 (eight bits). The scale is expressed in channel (ch) units. Further, b indicates the distribution of lymphocytes, c the distribution of monocytes and d the distribution of granulocytes. The distribution of debris, which is indicated at a, is composed of substances such as the membrane component of red blood cells. Often such debris is removed at the noise processing stage.

In order to analyze lymphocytes, an analytic area (a polygonal or elliptical window) $B_o$ which contains the lymphocyte distribution is set and data regarding the lymphocytes which belong to the area Bo is selected (extracted) from the measurement data. The lymphocyte data thus selected is subjected to calculation processing on the green fluorescence intensity $I_g$ and red fluorescence intensity $I_r$, and such operations as the calculation of positive ratio and the enumeration of the lymphocyte cell count are carried out. The results are displayed on a CRT and may be printed out by a printer.

The sample often is prepared from human blood. The reason for this is that blood reflects the conditions of human disease in a variety of ways and changes often appear in the pattern of cell groups in the scattered light cytogram or fluorescent-light cytogram in flow cytometry. There are several items of information regarding the various blood cells contained in human blood. Among these items of information, the positive ratio and raw data of the counts of various cells in the overall number of cells measured are employed in the examination of lymphocyte subsets in the prior art, as mentioned above. However, depending upon the disease, the positive ratio and the raw cell count do not always reflect the conditions of the disease accurately. For example, in the case of the disease AIDS, the ratio of the number of cells contained in the CD4 cell group of antibody classification and the ratio of the number of cells contained in the CD8 cell group to the total number of white blood cells often vary greatly depending upon individual differences or from one case to another. As a consequence, the condition of a disease cannot be grasped accurately based solely upon the positive ratio or the cell count (the percentage of a specific cell count in the total number of cells).

As mentioned above, there are several items of information regarding the various blood cells contained in human blood. Since the comparison of information often is performed on the basis of the positive ratio in the examination of lymphocyte subsets, it is difficult to make a direct comparison with already existing information (the range of normal values, for example), and there is the danger that the information will not be capable of being understood from a variety of aspects. In addition, though a comparison may also be made using measured cell count as a reference, the cell counts compared are diverse and the numerical values of the compared cell counts themselves are not always sufficiently reliable. When such is the case, the objectivity, interchangeability and reliability of the information are doubtful. Furthermore, if the measured cell count does not attain a predetermined value, as is possible with a specimen from a patient in which the cells are white blood cells and the condition of the patient's disease is being monitored following administration of an anti-cancer agent, a problem of low reliability arises in terms of the reliability of analysis. In addition, even though the specimen undergoing analysis is normal, the apparent cell count will be measured on the low side if the specimen is overly diluted at the time of preparation or if it cannot be taken up sufficiently because the specimen take-up operation is performed erroneously. This will make it necessary to prepare or measure the specimen again, thereby making it difficult to improve the efficiency of automation.

SUMMARY OF THE INVENTION

An object of the present invention is to provide a cell analyzing apparatus in which detection precision is improved in order that the condition of a disease may be understood more accurately.

Another object of the present invention is to provide a cell analyzing apparatus that is capable of discriminating an abnormal specimen and of so notifying the operator.

A further object of the present invention is to provide a cell analyzing apparatus in which the reliability and interchangeability of analytic information can be assured even if the cell count of a cell of interest contained in a measured sample does not attain a predetermined cell count.

A cell analyzing apparatus according to the present invention has a flow cell through which a specimen such as a cell suspension flows, a light source for irradiating the cells which flow through the flow cell with a light beam, cell light-information detecting means for detecting cell light information, which comprises one or a plurality of parameters, with regard to each of the cells irradiated with the light beam, cell light-information selecting means for selecting cell light information, which is indicative of a cell population of interest, from the cell light information detected by the cell light-information detecting means, cell light-information processing means for processing the cell light information detected by the cell light-information detecting means and the cell light information selected by the cell light-information selecting means, and output means for outputting results of processing executed by the cell-light information processing means, the apparatus comprising control specimen concentration information measuring means which uses a control specimen of a known concentration as the above-mentioned specimen for measuring the cell count of the specimen or the measurement time, subject specimen information measuring means which uses a subject specimen as the above-mentioned specimen for measuring the cell count of the specimen or the measurement time, subject specimen concentration correcting means, which uses the cell count or the measurement time regarding the control specimen obtained by the control specimen concentration information measuring means, for performing an operation to correct the cell count or measurement time of the subject specimen obtained by the subject specimen information measuring means, thereby obtaining the concentration of the subject specimen.

In accordance with the present invention, the cell count per unit volume (concentration) of a subject specimen, namely a specimen to be examined, can be obtained using a control specimen having a known concentration, and the cell light information can be processed using the concentration obtained. This makes it possible to obtain highly accurate examination results so that the condition of a disease can be understood with greater accuracy.

A cell analyzing apparatus according to another aspect of the present invention comprises a flow cell through which a cell suspension flows, a light source for irradiating the cell suspension which flows through the flow cell with a light beam, cell light-information detecting means for detecting cell light information, which comprises a plurality of parameters, with regard to each of the particle components of the cells contained in the particle suspension irradiated with the light beam, analytic-area setting means for setting an analytic area based upon one or a plurality of the parameters obtained by the cell light-information detecting means, cell light-information collecting means for collecting cell light information indicative of a cell population of interest within the analytic area set by the analytic-area setting means, cell light-information processing means for processing the cell light information detected by the cell light-information detecting means and the cell light information indicative of a cell population of interest collected by the cell light-information collecting means, and output means for outputting results of processing executed by the cell-light information processing means, the cell light-information processing means having specimen discriminating means for determining whether a specimen is normal or not.

In this cell analyzing apparatus, not only the positive ratio and the actually measured cell count, but also the absolute cell count, in which the measured cell count is calculated in terms of count per unit volume (1 mm$^3$ or 1 µl), is used in the processing of cell light information. This calculated overall cell count is compared with a preset normal range of values of each cell group. If the calculated cell count is outside the normal range of values, the specimen is judged to be abnormal and notification is given to this effect. On the basis of such notification, the operator is capable of performing a check to determine whether the specimen is indeed abnormal or whether the cause of the abnormality is the apparatus itself.

A cell analyzing apparatus according to still another aspect of the present invention has a flow cell through which a specimen such as a cell suspension, which is to undergo measurement, flows, a light source for irradiating the cells which flow through the flow cell with a light beam, cell light-information detecting means for detecting cell light information, which comprises one or a plurality of parameters, with regard to each of the cells irradiated with the light beam, cell light-information selecting means for selecting cell light information, which is indicative of a cell population of interest, from the cell light information detected by the cell light-information detecting means, cell light-information processing means for processing the cell light information detected by the cell light-information detecting means and the cell light information selected by the cell light-information selecting means, and output means for outputting results of processing executed by the cell-light information processing means, the apparatus comprising control specimen measuring means which uses a control specimen of a known concentration as the above-mentioned specimen for measuring the cell count of a cell of interest in the control specimen, subject specimen measuring means which uses a subject specimen as the above-mentioned specimen for measuring the cell count of the cell of interest in the subject specimen under measurement conditions identical with conditions under which the control specimen was measured, and cell-count coordinating means for making the cell count of the subject specimen obtained by the subject specimen measuring means agree, by means of an operation, with the cell count of the control specimen obtained by the control specimen measuring means.

In this cell analyzing apparatus, a cell count $N_0$ of a cell of interest contained in the control specimen is measured beforehand by the control specimen measuring means, and a cell count n of the cell of interest contained in the subject specimen to undergo examination is measured under measurement conditions identical with those under with the control specimen was measured. The cell count n of the subject specimen is then multiplied by $N_0/n$ so that the cell count of the subject specimen can be made to agree with the cell count $N_0$ of the control specimen. As a consequence, even if the measured cell count of the subject specimen is lacking, i.e., is less than the cell count of the control specimen serving as the reference, the cell count of the subject specimen can be made to agree with the cell count of the control specimen particularly in a case where the subject specimen is normal but the cell count is low for some unknown reason, or in a case where the specimen is that of a patient undergoing treatment of white blood cells. Moreover, the cell count of the subject specimen is made to coincide with the cell count obtained from a control specimen whose concentration is already known, so that a comparison of information and the processing of information are always carried out after the cell count of the cell population to be analyzed is made a constant, thereby making it possible to obtain interchangeability, objectivity and reliability of data without impeding the automation of analysis and improvements in the efficiency thereof.

Other features and advantages of the present invention will be apparent from the following description taken in conjunction with the accompanying drawings, in which like reference characters designate the same or similar parts throughout the figures thereof.

DESCRIPTION OF THE PREFERRED EMBODIMENT

Figure 1:
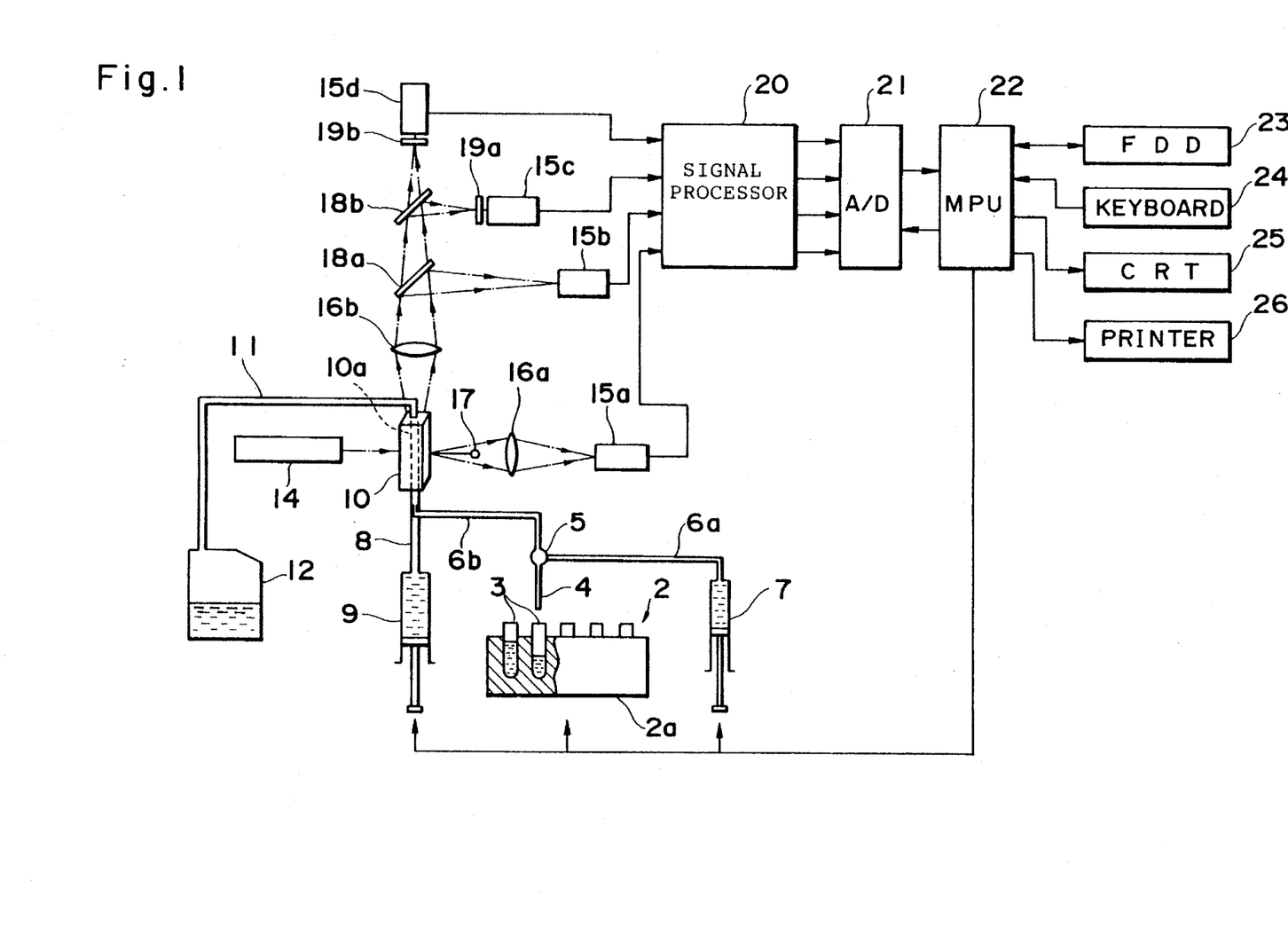
FIG. 1 is a block diagram for describing the construction of a cell analyzing apparatus.

FIG. 1 is a block diagram illustrating the construction of a cell analyzing apparatus. The apparatus includes an auto-sampler 2 for supplying samples. The auto-sampler 2 has a sample rack 2a holding a plurality of sample vessels 3 each filled with a sample. The sample rack 2a is driven by a drive mechanism (not shown) in such a manner that one of the sample vessels 3 filled with a sample that has been designated is positioned directly below a sample suction tube 4. The auto-sampler 2 has a shaking mechanism and a cooling mechanism (neither of which are shown). These mechanisms serve to shake the samples periodically and to maintain the samples filling the sample vessels 3 at a low temperature (e.g., 4°~10° C.).

The sample suction tube 4 is connected to one port of a three-way valve 5. Sample feed tubes 6a, 6b are connected at one end thereof to respective ones of the other two ports of three-way valve 5. Accordingly, communication can be established between sample feed tube 6a and sample suction tube 4 or between sample feed tubes 6a and 6b. The other end of sample feed tube 6a is provided with a sample pump 7, and the other end of sample feed tube 6b is open to a sheath-fluid feed tube 8.

The sheath-fluid feed tube 8 has two ends, one connected to a feed pump 9 and the other to a flow cell 10. The flow cell 10 is composed of quartz glass or the like and has an internal flow channel 10a in which a sheath flow is formed. Blood cells (or particles) contained in the sample are made to flow in single file along the central axis of the flow channel 10a by hydrodynamic focusing.

The liquid which has flowed out of the flow cell 10 is introduced to a waste tube 11 so that it may be collected by a waste tank 12. The cell analyzing apparatus has a sheath-fluid tank (not shown) by which the sample pump 7 and feed pump 9 are replenished with the sheath fluid. It is particularly advantageous if the pumps 7, 9 are syringe pumps. Furthermore, the feed system inclusive of the auto-sampler 2 and pumps 7, 9 is capable of being closed tightly to prevent biological hazards.

A laser (light source) 14 and photodetectors 15a, 15b, 15c, 15d are arranged about the flow cell 10. The laser beam from a laser 14 irradiates the cells (or particles) that flow through the flow channel 10a. The irradiated cells (or particles) emit signal light, part of which is forward-scattered light that is condensed by a lens 16a so as to impinge upon the photodetector 15a. A beam blocker 17 is provided to prevent the laser beam from impinging upon the photodetector 15a directly.

The irradiated cells emit 90° side-scattered light as well, and this light is condensed by a lens 16b. Part of this signal light is reflected by a dichroic mirror 18a so as to impinge upon the photodetector 15b, which is for detecting 90° side-scattered light. Part of the light which has passed through the dichroic mirror 18a is reflected by one more dichroic mirror 18b so as to pass through a filter 19a and be received by the photodetector 15c, which is for green fluorescent light. The light which has passed through the dichroic mirror 18b passes through a filter 19b so as to be received by the photodetector 15d, which is for red fluorescent light. By way of example, an argon laser or helium-neon laser is employed as the laser 14, a photodiode as the photodetector 15a for the forward-scattered light, and photomultiplier tubes as the other detectors 15b, 15c, 15d.

The photodetectors 15a, 15b, 15c, 15d produce output signals indicative of the light received. These signals are amplified and have noise eliminated by a signal processing circuit 20, after which the resulting signals are converted into digital signals by an analog/digital (A/D) converter 21. The digital signals are accepted by an MPU (microprocessing unit) 22.

The MPU 22 has several functions, which can be broadly classified as a function relating to automatic setting of a window, a function for storing measured cell count, and a function for correcting the cell count by an arithmetic operation. Other functions of the MPU 22 are a function for analyzing fluorescence with regard to light information indicative of a cell population of interest, and a function for controlling the sample pump 7, the feed pump 9 and the auto-sampler 2.

A floppy-disk drive 23, a keyboard 24, a CRT 25 and a printer 26 are connected to the MPU 22. The floppy-disk drive 23 preserves measurement conditions (protocols), measurement data, etc. by storing them on a floppy disk, and reads this information from the floppy disk. The keyboard 24 is for selecting protocols, setting a window and inputting other commands to the MPU 22. The CRT 25 is for monitoring the state of measurement. The printer 26 prints out the results of processing executed by the MPU 22. Examples are a cytogram, a histogram, etc.

The operation of a first embodiment performed using the cell analyzing apparatus constructed as set forth above will now be described with reference to the flowcharts of FIGS. 2 and 3.

First, samples that have been treated in line with the particular purpose of analysis are introduced to the respective sample vessels 3, which are then mounted in the sample rack 2a. For example, a sample to be analyzed for lymphocyte subsets is obtained by causing OKT 4 monoclonal antibody, which is labeled with fluorescein isothiocyanate (FITC) for green fluorescence, and OKT 8 monoclonal antibody, which is labeled with phycoerythrin (PE) for red fluorescence, to react with the patient's blood and then subjecting the result to hemolysis.

When the power supply of the cell analyzing apparatus is turned on, a program is read in the MPU 22 from a ROM (not shown) and the system is started up [step (hereinafter abbreviated as "ST") 1]. In a case where the object of measurement is a control specimen such as a blood-cell control, i.e., if a sample whose concentration has already been measured using a blood-cell counter or the like is measured by the apparatus of this invention ("YES" at ST 2), a protocol is selected and set by the operator or automatically in dependence upon the classification of the control specimen (ST 3). Measurement conditions, such as the detection gain of the photodetectors 15a, 15b, 15c, 15d and parameters for arithmetically correcting the output signals from these photodetectors constitute the content of the protocol selected. The reason for this is that the methods of treating a sample differs depending upon the purpose of measurement. For example, since the reactivities between cells and the monoclonal antibodies used in treatment differ from one another, it is necessary to change the detection gain of the photodetectors 15a, 15b, 15c, 15d. Further, since the manner in which each monoclonal antibody bonds with the fluorescent dye differs in each case, it is necessary to change also the parameter for the arithmetic correction in dependence upon the mode of bonding.

Next, an analytic region (window) is set manually (ST 4) in order to measure a specific cell (a pseudo-lymphocyte, for example) contained in the control specimen. Measurement of the control specimen is carried out using a blood-cell control such as Para Tech (Streck laboratories, Inc.). The blood-cell control has a cell count that is already known. In addition, such optical characteristics as the intensity of scattered light resemble those of human blood cells. A blood-cell control of this kind is convenient for setting the analytic area and for cell-count processing. This blood-cell control is measured as the sample (ST 5). At the end of measurement, the number of cells in the aforesaid analytic area is counted (ST 6). If necessary, automatic window-setting processing is executed using data obtained by measurement, and the analytic area set manually is corrected. The number of cells contained in the corrected analytic area is counted. In either case, let $N_0$ represent the counted number of cells of the specific type contained in the control specimen (i.e., the number of cells in the analytic area).

The processing for setting the window automatically is processing for demarcating the cell populations in a cytogram of the kind shown in FIG. 11. The demarcated area obtained for each cell population (or for a specific cell population) by this demarcation is adopted as a window or analytic area. For the details, see the specification of U.S. application Ser. No. 07/377,930 or EP-A-350873.

If necessary, the cell count $N_0$ obtained with regard to the control specimen is stored in a memory associated with the MPU 22 (ST 7). If it appears that the cell count $N_0$ obtained is unsuitable in consideration of the known concentration (the cell count per unit volume) of the control specimen, then measurement processing is repeated from ST 4 onward.

If it is determined at ST 2 that a control specimen is not to be measured (for example, if measurement of a control specimen has already been completed and the analytic results have already been stored in the memory), then the selection and setting of a protocol are carried out at ST 8, whence the program proceeds to ST 10.

At the end of measurement and analysis of the control specimen, the program proceeds to ST 9, at which a selection is made as to whether or not to use the same protocol If the decision is "NO", the program proceeds to the processing of ST 8, where the protocol is changed. If the decision at ST 9 is "YES", the program proceeds to ST 10. This step calls for the operator to select or not select automatic window-setting processing. If the decision is "NO", the program proceeds to ST 13 (FIG. 3); if "YES", the program proceeds to ST 11. It is determined at ST 11 whether a new measurement is to be taken. In case of a subject specimen, namely a specimen to undergo examination, that is of the same classification as a specimen measured previously, the analytic area that was entered at the time of the previous measurement or the analytic area that was obtained by analytic processing is read out of the memory and set (ST 12). In case of a new measurement, the analytic area is set manually (ST 13). Thereafter, measurement of the subject specimen to undergo examination starts (ST 14).

To measure a subject specimen, the sample rack 2a is driven in such a manner that the sample vessel 3 containing the sample that is to be measured first is brought into position immediately below the sample suction tube 4. The three-way valve 5 is then changed over so as to communicate the sample suction tube 4 and the sample feed tube 6a, the sample suction tube 4 is lowered into the sample vessel 3 and the sample pump 7 is driven to the suction side to draw the sample into the sample feed tube 6a. Next, the three-way valve 5 is changed over to communicate the sample feed tubes 6a and 6b, and the sample pump 7 is driven to the feed side to feed the sample to the feed tube 8. Meanwhile, the feed pump 9 is driven to the feed side so that the sheath fluid is feed to the flow cell 10. A sheath flow is formed within the flow channel 10a, and the cells flow in single file along the central axis of the flow channel 10a as a result of hydrodynamic focusing. The cells are irradiated with the laser beam and the forward-scattered light intensity $I_0$, 90° side-scattered light intensity $I_{90}$, green fluorescence intensity $I_g$ and red fluorescence intensity $I_r$ are measured for individual cells via the respective photodetectors 15a~ 15d, signal processing circuit 20 and A/D converter 21. The items of cell light information obtained by these measurements are successively stored on a floppy disk or the like as necessary.

It is determined (ST 15) whether absolute cell count is to be measured. Measurement of absolute cell count refers to obtaining, by arithmetic operation, the cell count per unit volume (concentration), as in the manner of cells/μl or cells/mm$^3$, with regard to a sample of blood cells.

It will suffice for the operator to enter in advance whether measurement of absolute cell count is to be carried out.

If it is determined that absolute cell count is to be measured, the program proceeds to ST 16, at which automatic window setting and computation of concentration (absolute cell count) are performed. In automatic window setting, demarcation of cell populations is carried out based upon the cytogram of data obtained by measurement, as mentioned earlier.

In computation of concentration, the count of a demarcated specific cell population (lymphocytes, for example) per unit volume is calculated (calibrated) using measurement data relating to the same cell population in the control specimen. In measurement of a sample of the control specimen, let $T_0$ sec represent the time required to obtain a cell count of $N_0$ cells. These items of data $N_0$, $T_0$ are obtained beforehand by the processing of ST 4~ST 6. The control specimen is a blood-cell control or the like, as set forth above, the number of cells of a specific type contained in this specimen is counted in advance by a blood-cell counter, and the concentration (the cell count per unit volume) $C_0$ of this specimen is known.

Methods of computing the concentration C of the subject specimen are of two types, which will now be described.

Figure 4:
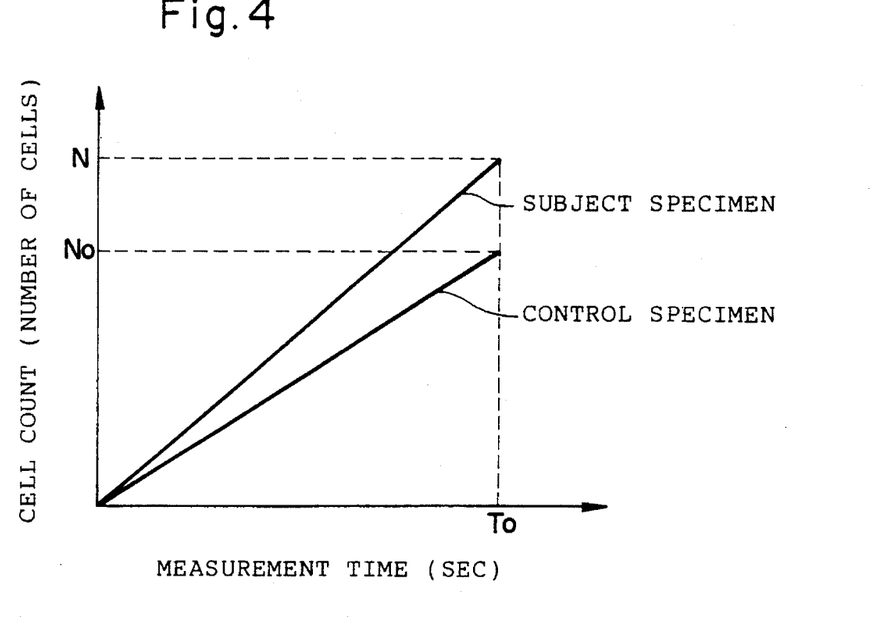
FIG. 4 is a graph illustrating the relationship between measurement time and cell count for a case where measurements of identical lengths of time are taken in calibration.

The first method of computation is as illustrated in FIG. 4. Specifically, let $T_0$ sec represent the time required to obtain the cell count of $N_0$ cells in measuring the sample of the control specimen, and let N represent the cell count of the subject specimen, where N is obtained by a measurement performed for a period of time identical to $T_0$ sec. The concentration C of the subject specimen under examination will then be represented by the following equation using the concentration $C_0$ of the control specimen:

$$C=C_0\times(N/N_0) \qquad (1)$$

Figure 5:
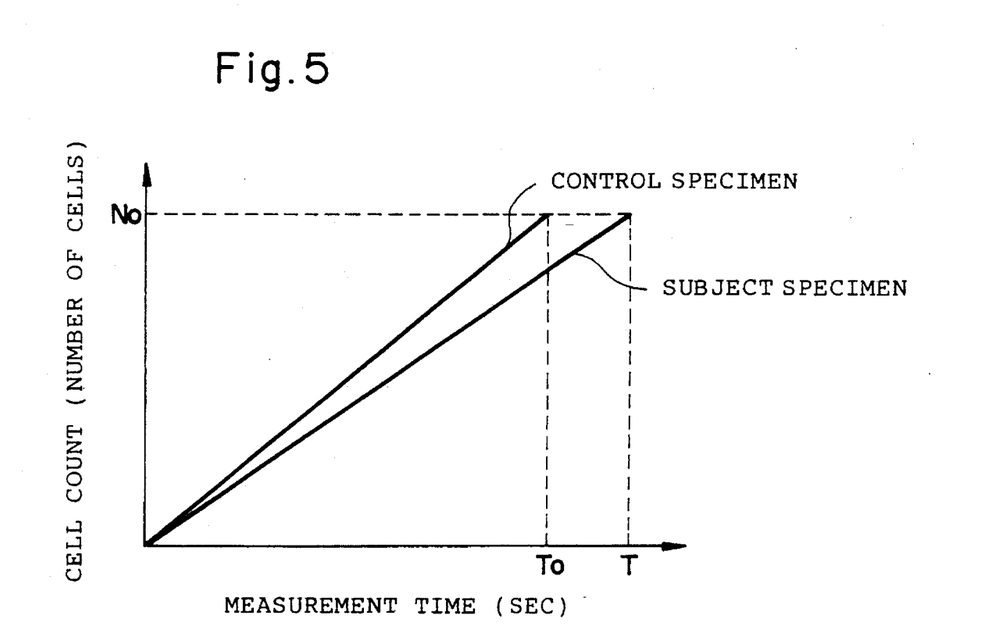
FIG. 5 is a graph illustrating the relationship between measurement time and cell count for a case where measurements of identical cell counts are taken in calibration.

The second method of computation is as illustrated in FIG. 5. Specifically, let T sec represent the period of time the subject specimen must be measured in order to obtain a cell count of $N_0$. The concentration C of the subject specimen will then be represented by the following equation:

$$C=C_0\times(T_0/T) \qquad (2)$$

In adjustment of the sample from the subject specimen, blood collected from a human being is diluted in a pretreatment. In adjustment of a sample from the control specimen also, the same pre-treatment as that used for the subject specimen is carried out and the control specimen is diluted at the same dilution ratio. If the sample of the subject specimen and the sample of the control specimen are prepared under identical conditions in this manner, then the concentration C of the subject specimen can be found utilizing the known concentration $C_0$ of the control specimen in either Eq. (1) or (2) above.

In a case where the measurement of absolute cell count is not performed, automatic window-setting processing is executed (ST 19) and the cells in the prescribed window (analytic area) thus set are subjected to analysis of their fluorescent characteristics, described below.

Fluorescent characteristics are analyzed (ST 17, ST 20) based upon the data processed at ST 16 or ST 19, respectively. This analysis involves creating a histogram for each of the green and red fluorescent-light intensities, for example, and calculating the positive ratio based upon these histograms. In the analysis of the fluorescent characteristics at ST 17, use is made of the concentration $C_0$ obtained at ST 16. In the analysis of the fluorescent characteristics at ST 20, direct use is made of the cell count obtained by measurement.

The results of analyzing the fluorescent characteristics are displayed on the CRT 25 (ST 18, ST 21) in conformity with the respective modes and they are printed out by the printer 26 (ST 22). This is followed by ST 23, at which the MPU 22 determines whether there is still a sample to be measured. If there is, the program returns to step S9; if there is not, the measurement operation is terminated (ST 24).

Figure 6:
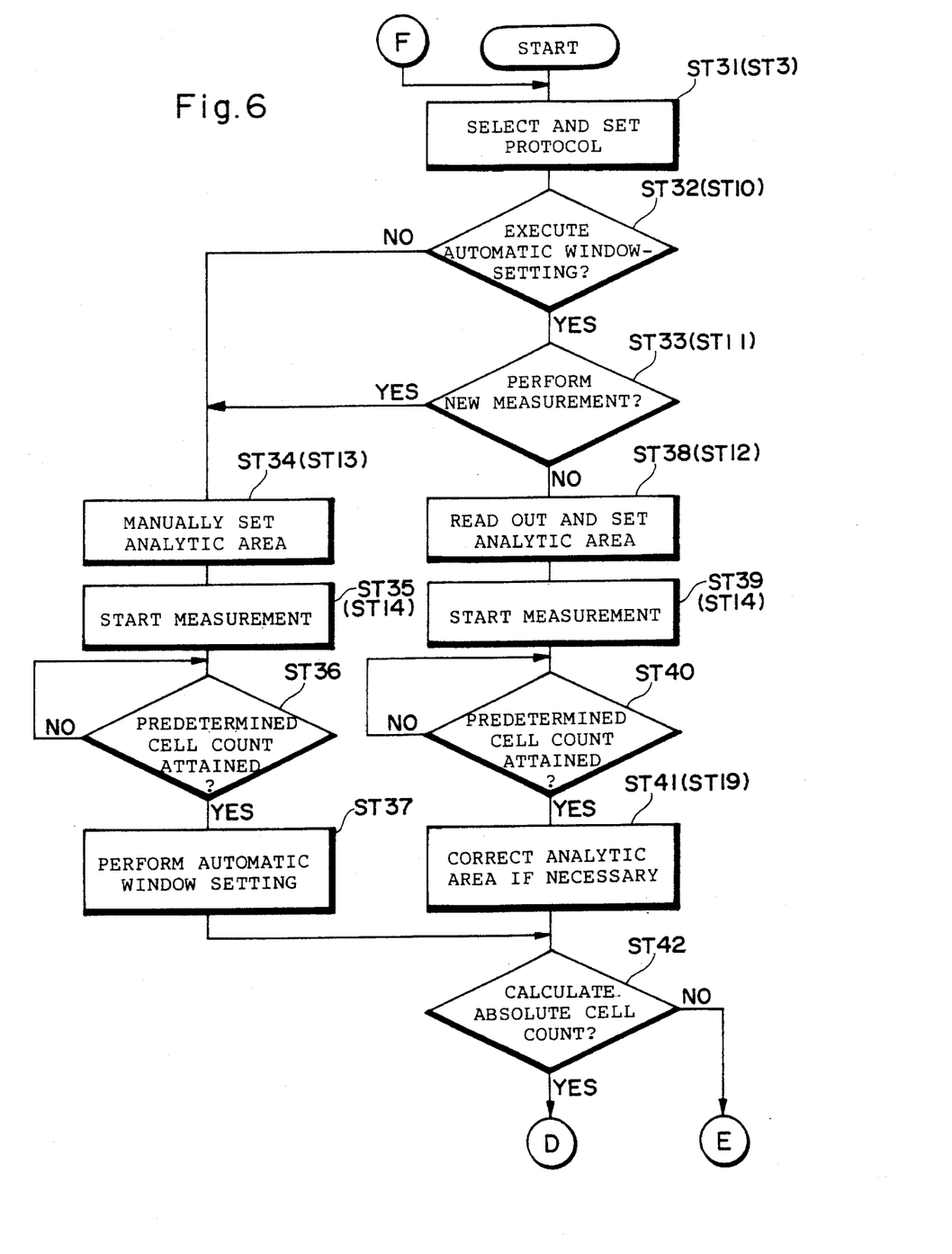
FIGS. 6 and 7 are flowcharts for describing the operation of a second embodiment.
Figure 7:
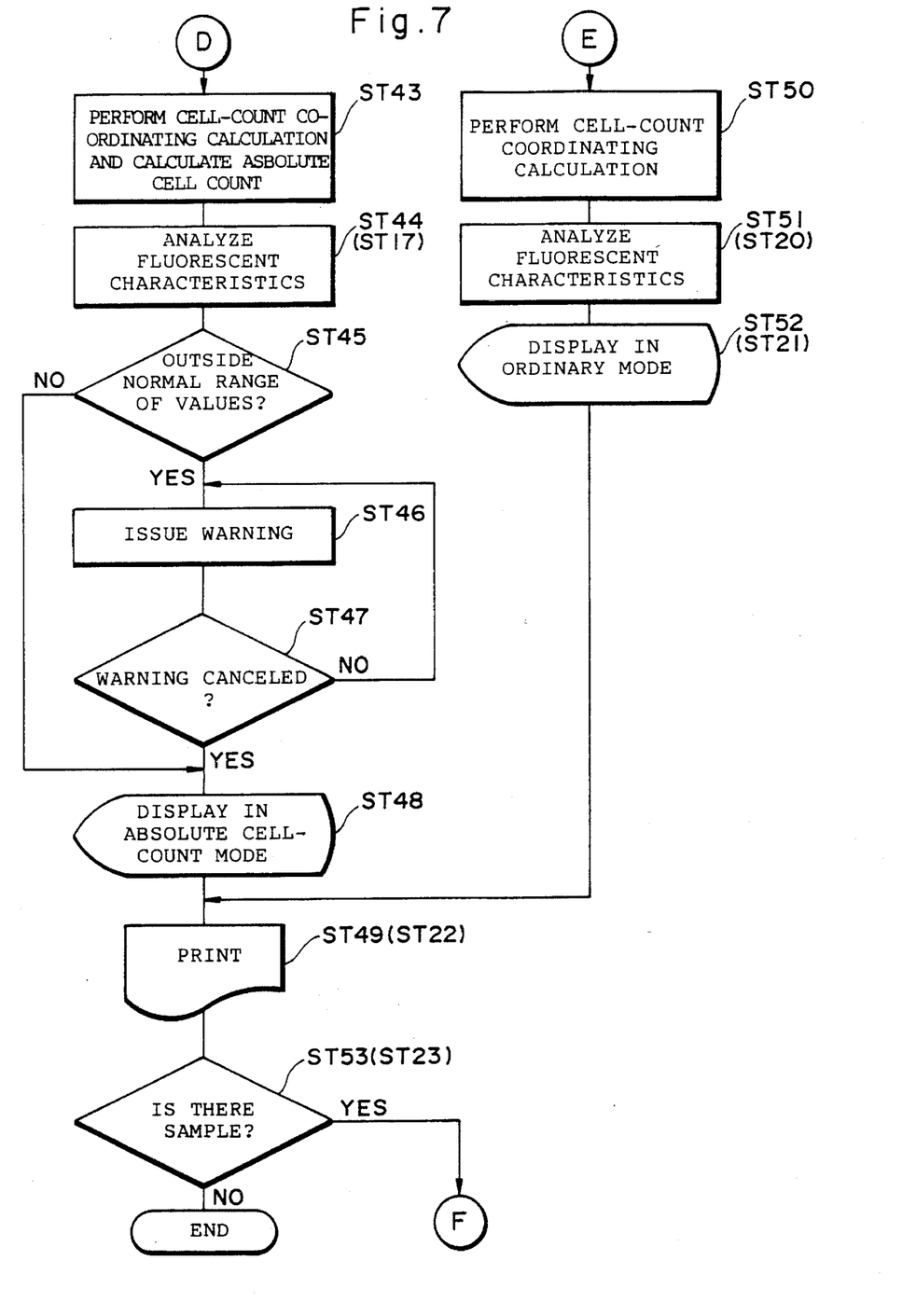

The operation of a second embodiment of the invention will be described with reference to the flowcharts shown in FIGS. 6 and 7. In this embodiment also, the construction of the automatic cell analyzing apparatus shown in FIG. 1 is utilized as is. In FIGS. 6 and 7, processing steps identical with those shown in FIGS. 2 and 3 have the same step numbers appended thereto.

Samples of subject specimens are prepared in a manner similar to that described above, the prepared samples are introduced to respective sample vessels 3, and the sample vessels 3 are mounted in the sample rack 2a. When the power supply of the apparatus is turned on, a program is read in to the MPU 22 from the ROM and the system is started up, just as described earlier. A protocol suited to the sample is selected and set (ST 31) in conformity with the sample measured.

Next, it is determined (ST 32) whether the operator has made an input from the keyboard 24 to the effect that automatic window setting is to be performed. If the answer at this step is "YES", the program branches to ST 33; otherwise, the program branches to ST 34. Whether or not a new measurement is to be performed is determined at ST 33 in accordance with an input entered by a key pressed by the operator. The program proceeds to step S34 if the decision is "YES and to step ST 38 if the decision is "NO.

Using the keyboard 24 at ST 34, the operator sets a window B (or an analytic area $B_0$) in the $I_{90}$ (90° side-scattered light intensity)-$I_0$(forward-scattered light intensity) cytogram (see FIG. 11). When the window B has been set, measurement starts (ST 35). Measurement processing is carried out in exactly the same manner as that in the operation of the first embodiment.

The second embodiment relates to a cell analyzing apparatus having a function for determining whether a characteristic (e.g., the positive ratio) or the number of cells of a specific classification contained in the analytic area resides in a normal range. Accordingly, it is necessary that the number of cells contained in the analytic area be made to agree with a predetermined number $n_0$. This predetermined number $n_0$ is decided by normality/abnormality judgment criteria.

As described earlier, the scattered light from individual cells is detected to obtain light information (data) indicative of the cells. In measurement of such light information (data), it is determined, for each item of data obtained from individual cells, whether the item of data belongs to the set window (or analytic area), and the cells whose data belongs to the window are counted. It is determined at ST 36 whether the value of the cell count has reached $n=n_0+\alpha$ (where $\alpha$ is a suitable number), which is greater than the predetermined number $n_0$. The program proceeds to S37 if the answer is "YES", and measurement is continued if the answer is "NO".

When measurement ends, automatic window-setting processing is executed and a correct analytic area (final demarcation) is set based upon the data obtained by measurement. Statistical calculations and computations regarding various parameters are performed with regard to the cell light information residing in the analytic area that has been set. Even if the set analytic area is smaller than the window B set earlier, the number of cells within this set analytic area will not be smaller than the predetermined number $n_0$. The reason for this is that the number n of measured cells has been set to be larger by the suitable number $\alpha$.

At ST 38, the analytic area $B_0$ obtained by the immediately preceding measurement is set in the $I_{90}$-$I_0$ cytogram (see FIG. 11). Measurement then starts (ST 39) in the same manner as at ST 35, the number of cells which fall in the analytic area $B_0$ are counted, and it is determined at ST 40 whether the number has attained the predetermined cell count n. When a "YES" decision is obtained at ST 40, measurement is ended and the program proceeds to ST 41.

Here the analytic area is corrected, if required, based upon the data obtained. Statistical calculations and computations regarding for parameters are performed with regard to the cells which reside within the corrected analytic area (the final demarcation).

Following ST 37 or ST 41, it is determined at ST 42 whether absolute cell count is to be computed. In the present apparatus, the sample pump 7 and the feed pump 9 are of the syringe type, as illustrated schematically in FIG. 1. As a consequence, the volume of the sample used in measurement may be obtained based upon the time from the start to the end of measurement, and it is possible for the cell count obtained by measurement to be calculated in terms of cell count per unit volume, i.e., per 1 mm$^3$ (1 μl). This is the absolute cell-count computation. The absolute cell count can be obtained using Eq. (1) or (2) above. Whether or not the computation of absolute cell count is performed is decided by an input made by the operator.

Figure 9A:
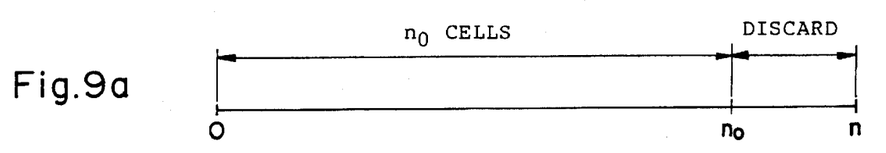
FIGS. 9a through 9c are diagrams for describing cell-count coordinating processing.
Figure 9B:
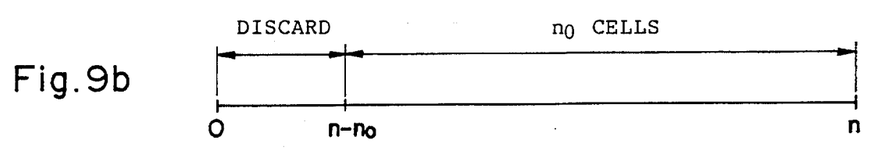
Figure 9C:
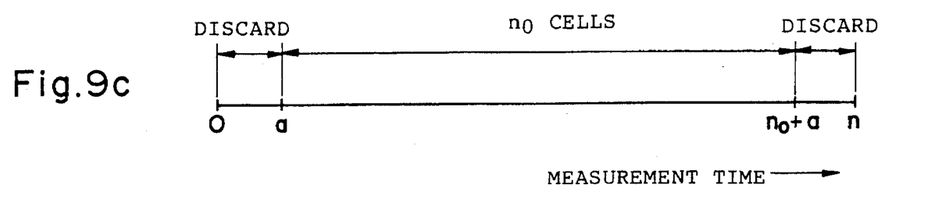

If a "YES" decision is rendered at ST 42, the program proceeds to ST 43. Here a cell-count coordinating computation and an absolute cell-count computation are carried out. The processing for coordinating cell count involves discarding superfluous cell data in such a manner that the number of cells contained in the analytic area becomes equal to the predetermined number $n_0$ mentioned above. This can be done in three ways. For example, in one way, as shown in FIG. 9a, data indicative of cells up to a count of $n_0$ from the start of measurement is taken as being valid, and the remaining data is taken as being invalid. In a second approach, as shown in FIG. 9b, data indicative of cells up to $n-n_0$ from the start of measurement is treated as being invalid, and the remaining data is treated as being valid. According to a third approach, as illustrated in FIG. 9c, data indicative of $n_0$-number of cells over an intermediate period of the measurement time is taken as valid data, and the remaining data is treated as being invalid.

The cell count $n_0$ coordinated in this manner is calculated in terms of absolute cell count by the absolute cell-count computation described above.

Analysis of fluorescent characteristics is performed (ST 44) based upon the data regarding the cells of cell count $n_0$ (the absolute cell count) thus coordinated. In accordance with this analysis, a histogram is created for each of the green fluorescent-light intensity $I_g$ and red fluorescent-light intensity $I_r$, for example, the positive ratio is calculated and so is the absolute cell count for each antibody classification.

Figure 8:
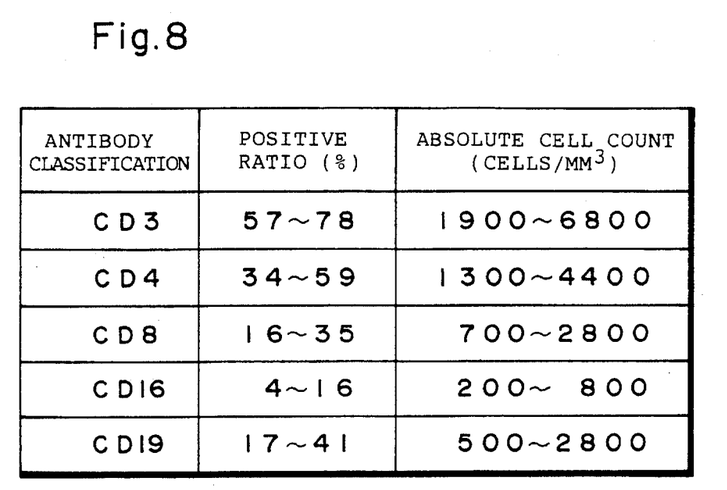
FIG. 8 is a reference-data table illustrating normal ranges used in judging specimens.

Next, it is determined whether the data obtained by such computation is normal. A reference range (data) for making this judgment is set in memory beforehand. FIG. 8 is a table showing various classifications of antibodies in lymphocytes, the normal range of positive ratio (%) of each classification and the normal range of absolute cell count (cells/mm$^3$) of each classification. A check is performed at ST 45 to determine whether the positive ratio and the absolute cell count regarding the various antibody classifications obtained by the processing of ST 44 fall outside the normal ranges.

If the answer obtained at ST 45 is "YES" (abnormal), i.e., if the data falls outside the range of normal values, then a warning is issued at ST 46. This warning can be issued using a printer, a CRT display, an liquid-crystal display, a light-emitting diode or a buzzer, etc. If the answer obtained at ST 45 is "NO" (normal) or the warning has been canceled by the operator (ST 47), the program proceeds to ST 48, where the absolute count of the data is displayed on the CRT display 25, after which the is printed out by the printer 26 (ST 49).

Thus, evaluation of the analyzed sample is carried out during the course of cell analysis and, if an abnormality is detected, notification of the fact is given. There are chiefly two causes of abnormality. One is that the sample itself is abnormal, and the other is that the sample is normal but is judged to be abnormal because of an abnormality in the operation of the cell analyzing apparatus. In the latter case, it is required that cell analysis be suspended and that the apparatus be inspected.

Though it cannot be determined whether the cause of an abnormality is the former or the latter described above, when an error is judged to have occurred the operator is so notified so that the abnormality can be called to his attention.

If it is determined at ST 42 that the absolute cell-count computation is not to be performed, a cell-count coordinating computation is performed in the manner described above. This is followed by ST 51, at which the fluorescent characteristics are analyzed in exactly the same manner as at ST 44. The results are displayed on the CRT 25 at ST 52. Here computation is performed and a display is presented using the cell count obtained by measurement. The results of analysis are printed out (ST 49).

After printing processing, it is determined whether there is still a sample to be measured (ST 53). If there is, the program returns to ST 31 and cell analyzing processing is repeated. If there are no further samples, then analytical processing ends.

Thus, in both the first and second embodiments, absolute cell count is found besides the cell count and positive ratio obtained by measurement, and the data are compared and judged. This makes it possible to improve the reliability of the data. In both embodiments (and in a third embodiment described below), a case is described in which a window is set for lymphocytes. However, the present invention is applicable also to a wide variety of samples, such as samples of monocytes, granulocytes and white blood cells.

Figure 10:
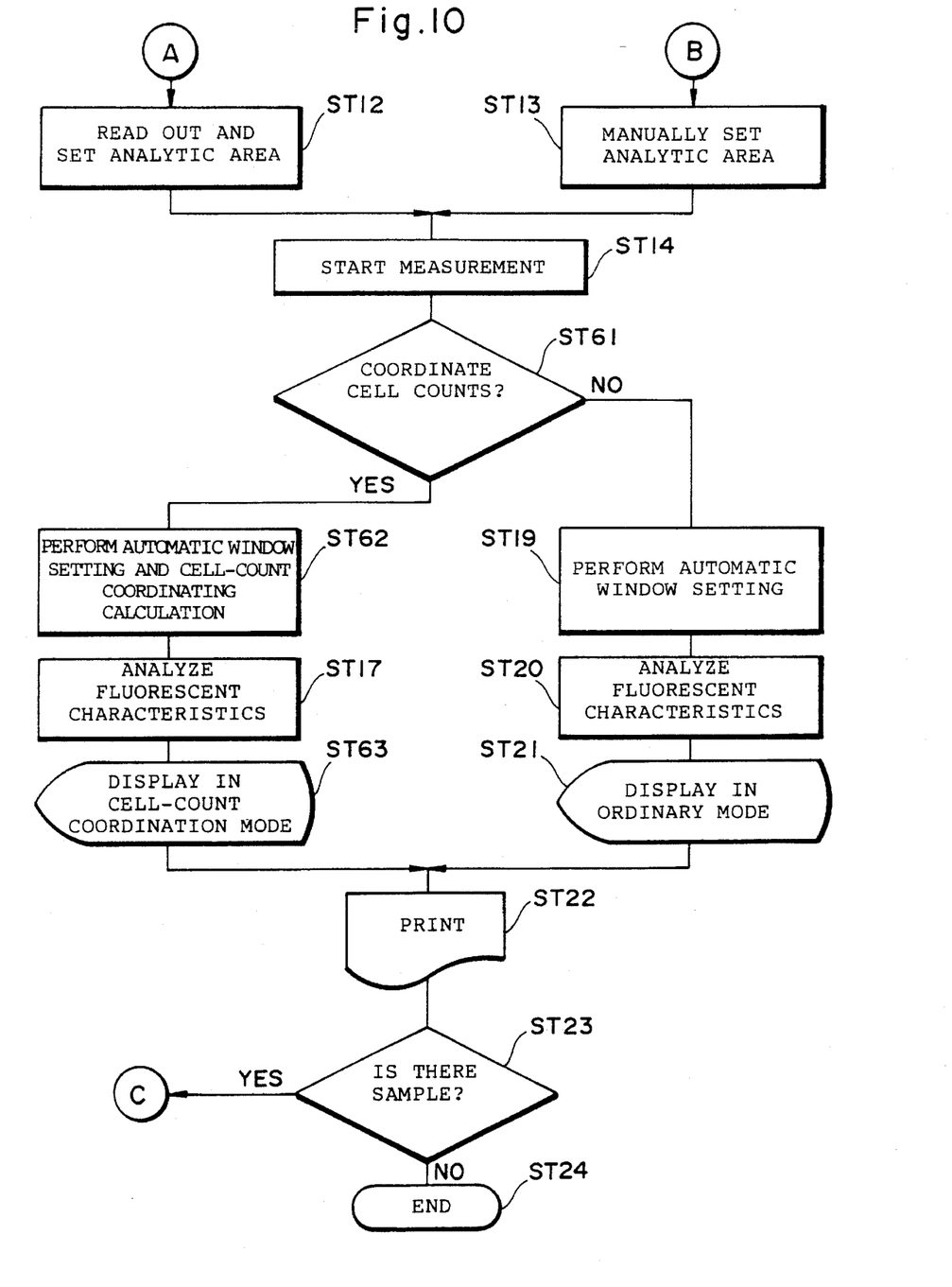
FIG. 10 is a flowchart for describing the operation of a third embodiment.

FIG. 10 illustrates a third embodiment. In this embodiment, the processing of FIG. 2 is utilized as is and the processing of FIG. 3 that follows the processing of FIG. 2 is replaced by the flowchart of FIG. 10, which includes processing for cell-count coordinating computation. The construction of the apparatus shown in FIG. 1 is capable of being utilized as is. In FIG. 10, processing steps identical with those shown in FIG. 3 are designated by the same step numbers.

In accordance with the second embodiment, coordination of cell count is performed by discarding data regarding superficial cells on the premise that data regarding a cell count larger than the predetermined number $n_0$ is obtained in measurement processing. However, in many samples of subject specimens, there are cases where the cell count does not attain the predetermined count $n_0$, even when all of the samples in the sample vessels 3 are measured, for some reason (e.g., when the sample is a blood sample collected from a patient who has been administered an anti-cancer agent to combat leukemia, a sample excessively diluted by erroneous pre-treatment, etc.). The third embodiment is so adapted that cell count can be coordinated even for such a sample in which the number of cells is small.

The operator uses the keyboard 24 to make an entry as to whether cell-count coordinating processing is to be executed. As a result, the program proceeds from ST 61 to ST 62 or ST 19 accordingly.

Automatic window-setting processing is executed at ST 62 based upon the measurement data obtained as set forth above. Let $B_1$ (see FIG. 11) represent the analytic area of white blood cells set by this processing. Thereafter, the program proceeds to processing for cell-count coordinating computation.

In a case where the number $n_0$ of cells contained in this analytic area $B_1$ is greater than the above-mentioned predetermined number $n_0$, the portion which exceeds the cell count $n_0$ is discarded by any of the methods shown in FIGS. 9a, 9b and 9c in order to make the cell count of the cells in the analytic area (final demarcation) $B_1$ equal to $n_0$.

The counting of the cells contained in the analytic area is carried out in concurrence with the measurement of light information from the individual cells in the manner described above. Even if there is a case in which the measured cell count does not attain the predetermined number $n_0$, measurement ends when the sample fed by the sample pump 7 is completely used up. The end of measurement is sensed as by a sensing switch provided in the sample pump 7. As for the comparison with the sample of the control specimen, it is preferred that the cell count $N_0$ of the cells in the analytic area contained in the control specimen sample and the above-mentioned predetermined value $n_0$ be made equal.

Figure 2:
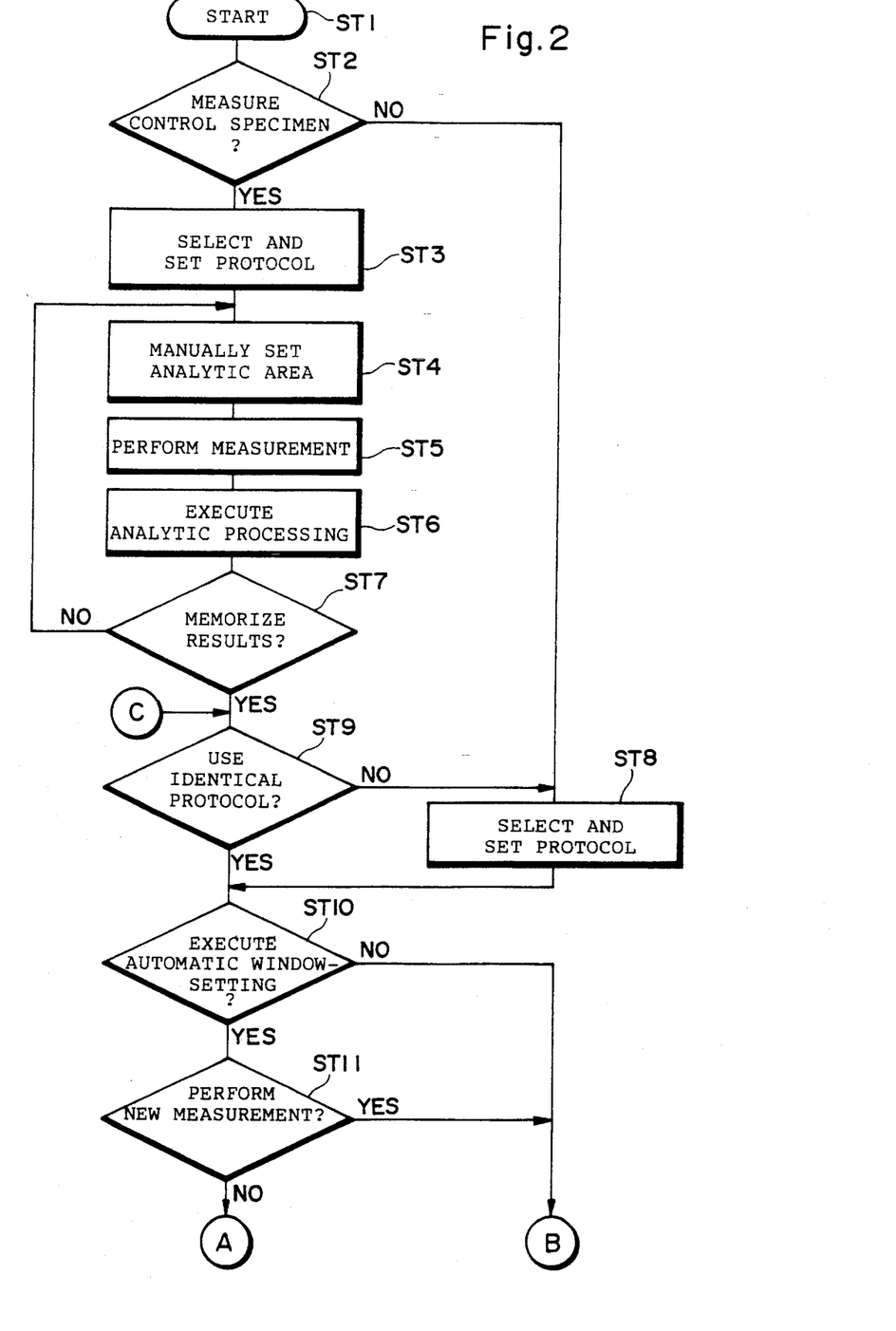
FIGS. 2 and 3 are flowcharts for describing the operation of a first embodiment.
Figure 3:
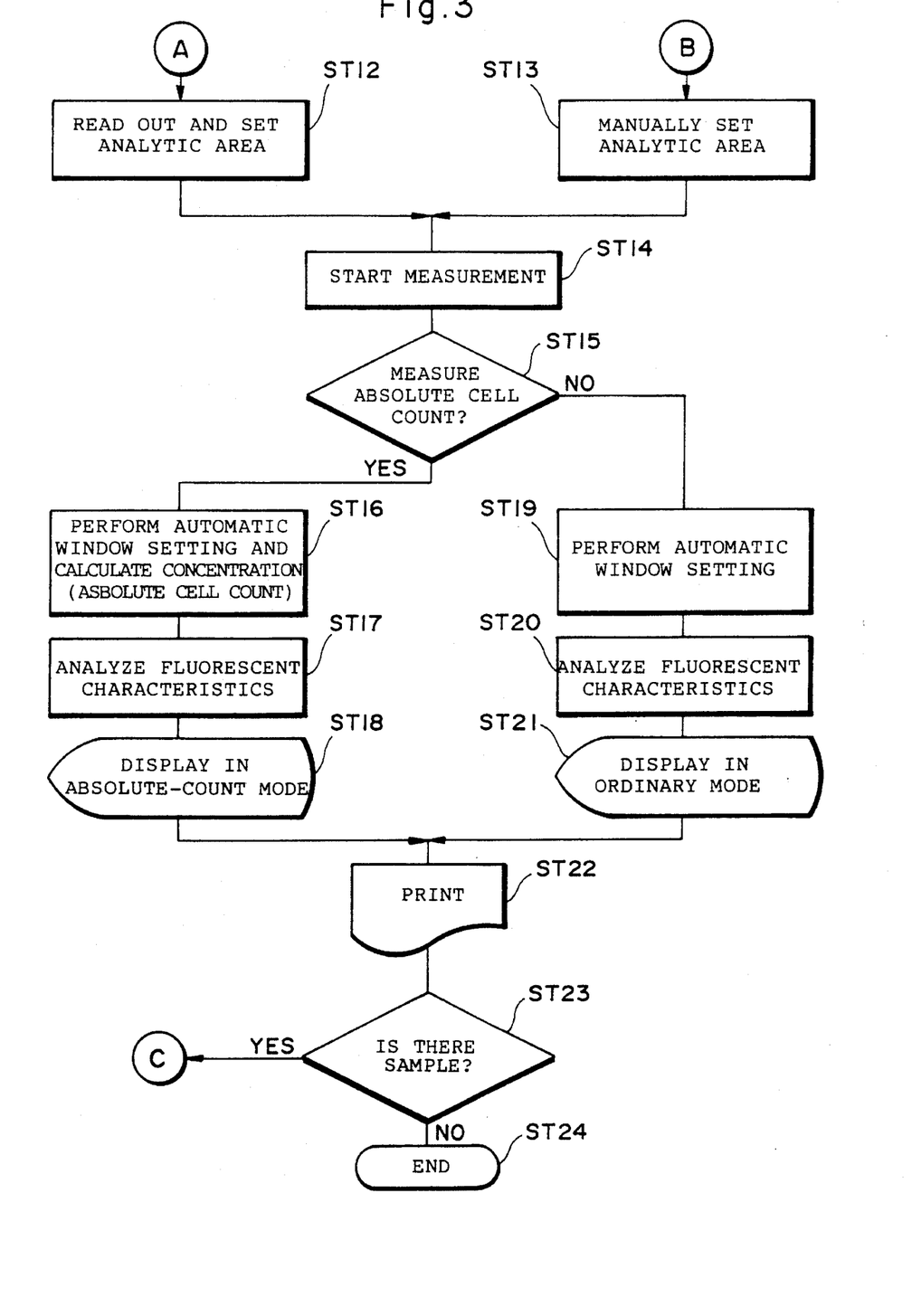

Accordingly, in a case where the obtained cell count $n$ does not attain the cell count $N_0=n_0$ even when the above-mentioned measurement is performed, the cell count $N_0$ stored at ST 7 in FIG. 2 is read out and the measured cell count $n$ is multiplied by the coefficient $\beta=N_0/n$ to achieve coincidence with the cell count $n_0$.

Accordingly, in a case where cell counts $n_1, n_2, \ldots, n_n$ of a plurality of cell groups (e.g., the above-mentioned antibody classifications CD3, CD4, CD8, etc.) are obtained as the result of analyzing specimens using a plurality of monoclonal antibodies in examination of lymphocyte subsets, these cell counts are multiplied by the coefficient $\beta$ to obtain $n_1 \cdot \beta, n_2 \cdot \beta, \ldots, n_n \cdot \beta$. As a result, in all cases the cell count of the subject specimen under examination is made to agree with the cell count $N_0$ of the control specimen serving as the reference.

It goes without saying that an arrangement can be adopted in which one cell analyzing apparatus is provided with all or any two of the processing operations for concentration computation in the first embodiment, normality/abnormality judgment of the second embodiment and cell-count coordination of the third embodiment.

As many apparently widely different embodiments of the present invention can be made without departing from the spirit and scope thereof, it is to be understood that the invention is not limited to the specific embodiments thereof except as defined in the appended claims.

What is claimed is:

1. A cell analyzing apparatus comprising:

a flow cell through which a specimen flows;

a light source for irradiating cells in the specimen flowing through said flow cell;

cell light-information detecting means for detecting cell light information as detected cell light information, said detected cell light information comprising at least one parameter for each cell irradiated with the light source;

cell light-information selecting means for selecting, as selected cell light information, cell light information from the detected cell light information;

cell light-information processing means for processing the detected cell light information and the selected cell light information;

control specimen concentration information measuring means for measuring a control cell count of a control specimen having a known concentration;

subject specimen information measuring means for measuring a subject cell count of a subject specimen; and subject specimen concentration correcting means for correcting the subject cell count, based upon the control cell count, to obtain the concentration of the subject specimen, output means for outputting results of at least one of processing by said cell-light information processing means, measuring by said control specimen concentration information measuring means, measuring by said subject specimen information measuring means, and correcting by said subject specimen concentration means;

wherein said subject specimen concentration correcting means obtains a concentration of the subject specimen, using information indicative of measurement time obtained by said control specimen concentration information measuring means, based upon a cell count of the subject specimen obtained over a measurement time identical to the measurement time obtained by said control specimen concentration information measuring means according to the formula $C=C_o \times (N/N_o)$;

wherein C represents the concentration of the subject specimen, $C_o$ represents the concentration of the control specimen, N represents the cell count of the subject specimen and $N_o$ represents the cell count of the control specimen.

2. The apparatus according to claim 1, wherein said subject specimen concentration correcting means uses a rate of dilution for correcting.

3. The apparatus according to claim 1, wherein said cell light-information processing means comprises specimen discriminating means for determining whether a specimen is normal.

4. The apparatus according to claim 1, further comprising:

control specimen measuring means which uses a control specimen of a known concentration for measuring a control cell count of a cell type of interest in the control specimen;

subject specimen measuring means which uses a subject specimen for measuring a subject cell count of the cell type of interest in the subject specimen under measurement conditions identical with conditions under which the control cell count was measured; and cell-count coordinating means for making the subject cell count and the control cell count agree.

5. A cell analyzing apparatus comprising:

a flow cell through which a specimen flows;

a light source for irradiating cells in the specimen flowing through said flow cell;

cell light-information detecting means for detecting cell light information as detected cell light information, said detected cell light information comprising at least one parameter for each cell irradiated with the light source;

cell light-information selecting means for selecting, as selected cell light information, cell light information from the detected cell light information;

cell light-information processing means for processing the detected cell light information and the selected cell light information;

control specimen concentration information measuring means for measuring a control measurement time of a control specimen having a known concentration;

subject specimen information measuring means for measuring a subject measurement time of a subject specimen; and subject specimen concentration correcting means for correcting the subject measurement time, based upon the control measurement time, to obtain the concentration of the subject specimen, output means for outputting results of at least one of processing by said cell-light information processing means, measuring by said control specimen concentration information measuring means, measuring by said subject specimen information measuring means, and correcting by said subject specimen concentration means;

wherein said subject specimen concentration correcting means obtains the concentration of the subject specimen, using information indicative of a cell count obtained by said control specimen concentration information measuring means, based upon measurement time of the subject specimen needed to obtain a cell count identical with a cell count obtained by said control specimen concentration information measuring means according to the formula $C=C_o \times (T_o/T)$;

wherein C represents the concentration of the subject specimen, $C_o$ represents the concentration of the control specimen, $T_o$ represents the time required to obtain a particular number of cells in the control specimen, and T represents the time required to obtain the same number of cells in the subject specimen.

6. The apparatus according to claim 5, wherein said subject specimen concentration correcting means uses a rate of dilution for correcting.

7. The apparatus according to claim 5, wherein said cell light-information processing means comprises specimen discriminating means for determining whether a specimen is normal.

8. The apparatus according to claim 5, further comprising:

control specimen measuring means which uses a control specimen of a known concentration for measuring a control cell count of a cell type of interest in the control specimen;

subject specimen measuring means which uses a subject specimen for measuring a subject cell count of the cell type of interest in the subject specimen under measurement conditions identical with conditions under which the control cell count was measured; and cell-count coordinating means for making the subject cell count and the control cell count agree.

9. A cell analyzing method for use in a cell analyzing apparatus comprising:

a flow cell through which a specimen flows;

a light source for irradiating cells which flow through said flow cell with a light beam;

cell light-information detecting means for detecting cell light information, which comprises at least one parameter with regard to each cell irradiated with the light beam;

cell light-information selecting means for selecting cell light information indicative of a cell population of interest, from the cell light information detected by said cell light-information detecting means;

cell light-information processing means for processing the cell light information detected by said cell light-information detecting means and the cell light information selected by said cell light-information selecting means; and output means for outputting results of processing by said cell-light information processing means;

said cell analyzing method comprising the steps of:
(a) measuring a control cell count of a control specimen having a known concentration and used as the specimen to obtain control measurements;
(b) measuring a subject cell count of a subject specimen used as said specimen to obtain subject measurements; and
(c) obtaining a concentration of the subject specimen by correcting the subject measurements using the control measurements according to the formula $C=C_o \times (N/N_o)$;

wherein C represents the concentration of the subject specimen, $C_o$ represents the concentration of the control specimen, N represents the cell count of the subject specimen and $N_o$ represents the cell count of the control specimen.

10. A cell analyzing method for use in a cell analyzing apparatus comprising:

a flow cell through which a specimen flows;

a light source for irradiating cells which flow through said flow cell with a light beam;

cell light-information detecting means for detecting cell light information, which comprises at least one parameter with regard to each cell irradiated with the light beam;

cell light-information selecting means for selecting cell light information indicative of a cell population of interest, from the cell light information detected by said cell light-information detecting means;

cell light-information processing means for processing the cell light information detected by said cell light-information detecting means and the cell light information selected by said cell light-information selecting means; and output means for outputting results of processing by said cell-light information processing means;

said cell analyzing method comprising the steps of:
(a) measuring a control measurement time of a control specimen having a known concentration and used as the specimen to obtain control measurements;
(b) measuring a subject measurement time of a subject specimen used as said specimen to obtain subject measurements; and
(c) obtaining a concentration of the subject specimen by correcting the subject measurements using the control measurements according to the formula $C=C_o \times (T_o/T)$;

wherein C represents the concentration of the subject specimen, $C_o$ represents the concentration of the control specimen, $T_o$ represents the time required to obtain a particular number of cells in the control specimen, and T represents the time required to obtain the same number of cells in the subject specimen.

* * * * *